(12) United States Patent
Alarcon et al.

(10) Patent No.: US 10,905,162 B2
(45) Date of Patent: Feb. 2, 2021

(54) DEVICE AND METHOD FOR SENSING MASS AIRFLOW

(71) Applicant: Fontem Holdings 4 B.V., Amsterdam (NL)

(72) Inventors: Ramon Alarcon, Los Gatos, CA (US); Michael Starman, Los Gatos, CA (US)

(73) Assignee: Fontem Holdings 4 B.V., Amsterdam (NL)

( * ) Notice: Subject to any disclaimer, the term of this patent is extended or adjusted under 35 U.S.C. 154(b) by 421 days.

(21) Appl. No.: 14/899,103

(22) PCT Filed: Jun. 19, 2014

(86) PCT No.: PCT/US2014/043253
§ 371 (c)(1),
(2) Date: Dec. 16, 2015

(87) PCT Pub. No.: WO2014/205263
PCT Pub. Date: Dec. 24, 2014

(65) Prior Publication Data
US 2016/0366939 A1 Dec. 22, 2016

Related U.S. Application Data

(60) Provisional application No. 61/836,923, filed on Jun. 19, 2013.

(51) Int. Cl.
A24F 47/00 (2020.01)
A61M 11/04 (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ... A24F 47/008; A61M 11/042; A61M 15/06; A61M 2016/0021; A61M 2205/3334;
(Continued)

(56) References Cited

U.S. PATENT DOCUMENTS 3,548,841 A * 12/1970 Caughey .............. A24C 5/3406
131/175
4,660,510 A * 4/1987 Draper .................... F22B 1/165
122/31.1
(Continued)

FOREIGN PATENT DOCUMENTS

CN 1541577 A 11/2004
CN 102227175 A 10/2011
(Continued)

*Primary Examiner* — Dana Ross
*Assistant Examiner* — Ket D Dang
(74) *Attorney, Agent, or Firm* — Dykema Gossett PLLC

(57) ABSTRACT

A system, a method, a device and a computer program are provided for detecting and monitoring medium flow. The device comprises a flow sensor (350) that includes a thermopile (352), wherein the thermopile (352) may include a first thermocouple and a second thermocouple. The device can further comprise a microcontroller (340) that can be configured to generate a reference baseline and can further be configured to compare an output of the mass airflow sensor to the reference baseline (503). The heater element may comprise a heater resistor.

17 Claims, 10 Drawing Sheets

(51) Int. Cl.
*G01F 1/688* (2006.01)
*A61M 15/06* (2006.01)
*G01F 1/76* (2006.01)
*H05B 1/02* (2006.01)
*A61M 16/00* (2006.01)

(52) U.S. Cl.
CPC .............. *G01F 1/6888* (2013.01); *G01F 1/76* (2013.01); *H05B 1/0244* (2013.01); *A61M 2016/0021* (2013.01); *A61M 2205/3334* (2013.01); *A61M 2205/3368* (2013.01); *A61M 2205/8212* (2013.01); *H05B 2203/021* (2013.01)

(58) Field of Classification Search
CPC ... A61M 2205/3368; A61M 2205/8212; G01F 1/6888; G01F 1/76; H05B 1/0244; H05B 2203/021
USPC ....... 392/368, 386, 390, 394, 397, 389, 403, 392/404, 406; 131/328, 329, 330, 187, 131/273, 904, 194, 270, 271; 128/200.14, 128/200.17, 200.21, 200.22, 200.23, 128/203.12, 203.15, 204.18, 204.25, 128/203.27, 202.21, 202.27; 239/650, 239/102.1, 102.2, 338, 350, 135, 309, 239/340, 346, 373, 426, 433, 434; 219/494, 497, 499, 501, 505, 483, 485, 219/486, 492
See application file for complete search history.

(56) References Cited

U.S. PATENT DOCUMENTS

| | | | | |
|---|---|---|---|---|
| 4,947,875 A * | 8/1990 | Brooks | ................ | A24F 47/006 128/202.21 |
| 5,967,148 A * | 10/1999 | Harris | ................... | A24F 47/008 131/329 |
| 6,040,560 A * | 3/2000 | Fleischhauer | ......... | A24F 47/008 128/202.21 |
| 7,034,677 B2 * | 4/2006 | Steinthal | ................ | B82Y 30/00 128/903 |
| 2006/0172442 A1 | 8/2006 | Okabe et al. | | |
| 2006/0196518 A1 * | 9/2006 | Hon | ....................... | A24F 47/002 131/360 |
| 2007/0144514 A1 * | 6/2007 | Yeates | ............... | A61M 15/0086 128/203.15 |
| 2009/0090361 A1 * | 4/2009 | Gumaste | ........... | A61M 15/0085 128/203.15 |
| 2010/0163063 A1 * | 7/2010 | Fernando | .............. | A24F 47/008 131/184.1 |
| 2010/0242974 A1 * | 9/2010 | Pan | ........................ | A24F 47/008 131/273 |
| 2010/0307518 A1 * | 12/2010 | Wang | ................... | A24F 47/008 131/329 |
| 2011/0031419 A1 * | 2/2011 | Fukui | ................... | G08B 17/107 250/574 |
| 2011/0226236 A1 | 9/2011 | Buchberger | | |
| 2011/0265806 A1 * | 11/2011 | Alarcon | ................. | A24F 47/00 131/273 |
| 2012/0048266 A1 * | 3/2012 | Alelov | ................. | A61M 11/005 128/202.21 |
| 2012/0050750 A1 * | 3/2012 | Hays | ......................... | G01J 9/04 356/519 |
| 2012/0186594 A1 * | 7/2012 | Liu | ....................... | A24F 47/008 131/329 |
| 2012/0199146 A1 * | 8/2012 | Marangos | ............. | A24F 47/008 131/328 |

FOREIGN PATENT DOCUMENTS

| | | |
|---|---|---|
| CN | 202172847 U | 3/2012 |
| CN | 102970885 A | 3/2013 |
| EP | 1 618 803 A1 | 1/2006 |
| GB | 2468932 A | 9/2010 |
| JP | S63122963 A | 5/1988 |
| JP | 2004 516101 A | 6/2004 |
| JP | 2004 212103 A | 7/2004 |
| JP | 2005038058 A | 2/2005 |
| JP | 2012 506263 A | 3/2012 |
| WO | 2010/003480 A1 | 1/2010 |
| WO | 2011160788 A1 | 12/2011 |
| WO | 2013/060781 A1 | 5/2013 |

* cited by examiner

DEVICE AND METHOD FOR SENSING MASS AIRFLOW

CROSS-REFERENCE TO RELATED APPLICATIONS

This application claims the benefit of U.S. provisional application No. 61/836,923, filed 19 Jun. 2013, which is hereby incorporated by reference as though fully set forth herein.

FIELD OF THE DISCLOSURE

The present disclosure relates to a system, a method, a device, and a computer program for detecting and monitoring medium flow, including, e.g., gas flow, liquid flow, aerosol flow, or the like.

BACKGROUND OF THE DISCLOSURE

Electronic cigarettes, also known as e-cigarette (eCigs) and personal vaporizers (PVs), are electronic inhalers that vaporize or atomize a liquid solution into an aerosol mist that may then be delivered to a user. A typical eCig has two main parts—a battery part and a cartomizer. The battery part typically includes a rechargeable lithium-ion (Li-ion) battery, a light emitting diode (LED), and a pressure sensor. The cartomizer typically includes a liquid solution, an atomizer and a mouthpiece. The atomizer typically includes a heating coil that vaporizes the liquid solution.

In prior art eCigs, the pressure sensor is configured to sense a user's draw on the eCig and transmit an activation signal to the heating coil to vaporize the liquid solution. However, these pressure sensors can be large and costly. An unfulfilled need exists for a sensor that is capable of detecting a user's draw on an eCig, but which is small and uses little battery energy to operate.

The present disclosure provides a system, a method, a device and a computer program that meet the unfulfilled need, providing a small, low energy consumption device.

SUMMARY OF THE DISCLOSURE

According to one non-limiting example of the disclosure, a system, a method, a device and a computer program are provided for detecting and monitoring medium flow. The device comprises a flow sensor that includes a thermopile, wherein the thermopile may include a first thermocouple and a second thermocouple. The flow sensor may further include a reference element and a heater element. The reference element may comprise a reference resistor. The heater element may comprise a heater resistor.

The system comprises the flow sensor and a microcontroller. The microcontroller may comprise a microcomputer, a memory and an interface. The microcontroller may further comprise a real-time clock (RTC). The microcontroller may comprise an application specific integrated circuit (ASIC). The microcontroller is configured to receive sensor signals from the flow sensor and detect medium flow in a predetermined region. The microcontroller may be configured to monitor the medium flow as a function of time. The microcontroller may be configured to log medium flow data, including time and date data associated with the medium flow data. The medium may comprise an aerosol, a gas (e.g., air), a liquid, or the like. The microcontroller may be configured not only to turn ON/OFF a heater based on data, but to also adjust control parameters such as, e.g., a heater pulse width modulation (PWM) drive signal and/or an amount of liquid solution dispensed onto a heating surface. The control may be done proportionally to the flow data or according to an algorithm where flow data is a parameter. Additionally, the microcontroller may use flow data to determine flow direction and restrict or limit false activation of a heater, e.g., in case the user accidentally blows into the device.

The method may be implemented to detect medium flow in or proximate to a predetermined region. The method comprises receiving sensor signals, detecting changes in a temperature, and identifying a threshold-exceeding activity. The threshold-exceeding activity may comprise a shift in a temperature profile in the flow sensor above a predetermined threshold value.

The computer program may be provided on a computer-readable medium that, when executed on a computer, causes the method of detecting medium flow to be carried out. The computer-readable medium may comprise one or more code sections or segments that are configured to carry out the steps of the processes described herein, including the method of detecting medium flow.

In one embodiment, an electronic cigarette can comprise a body, an atomizer within the body, a microcontroller, a power supply within the body and electrically connected to the microcontroller and the atomizer, and a mass air flow sensor electrically connected to the microcontroller.

In another embodiment, an electronic cigarette can comprise a first housing and a second housing, an atomizer within the first housing, a microcontroller within the second housing and comprising a data acquisition circuit and an analog-to-digital converter, a power supply within the second housing and configured to be electrically connected to the microcontroller and the atomizer, and a flow sensor electrically connected to the microcontroller, wherein the first housing is configured to be coupled to the second housing.

In yet another embodiment, an electronic cigarette can comprise a housing, an atomizer within the housing, a microcontroller comprising a data acquisition circuit and an analog-to-digital converter, a power supply electrically connected to the microcontroller and the atomizer, and a flow sensor comprising a thermopile and a heater, and wherein the flow sensor is electrically connected to the microcontroller.

Additional features, advantages, and embodiments of the disclosure may be set forth or apparent from consideration of the detailed description and drawings. Moreover, it is to be understood that the foregoing summary of the disclosure and the following detailed description and drawings are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

Figure 1:
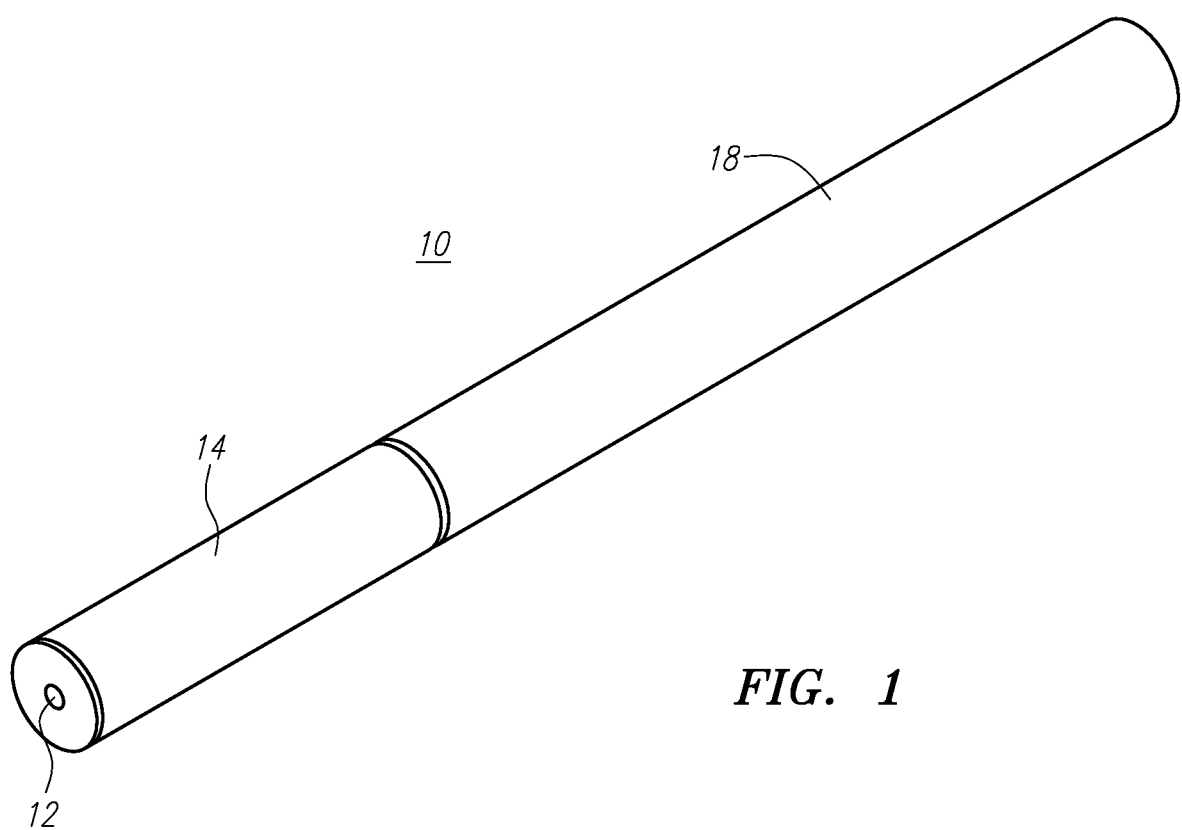
FIG. 1 shows an example of an eCig that is constructed according to an aspect of the disclosure.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

FIG. 1 shows an example of an eCig 10 that is constructed according to an aspect of the disclosure. The eCig 10 comprise a cartridge 14 and an eCig body 18. The cartridge 14 comprises an opening 12 through which aerosol may be delivered to a user. The cartridge 14 comprises a flavorant (not shown) and an atomizer (not shown). The flavorant may include, e.g., a liquid solution, a gel, a solid, or a gas that comprises molecules to be delivered in an aerosol to a user. The eCig body 18 includes a power supply (e.g., a rechargeable Li-ion battery) (not shown) and an LED (not shown). The eCig 10 includes a flow sensor device (not shown), which may include a microcontroller 20 (shown in FIG. 2) and a flow sensor 30 (shown in FIG. 3).

Figure 2:
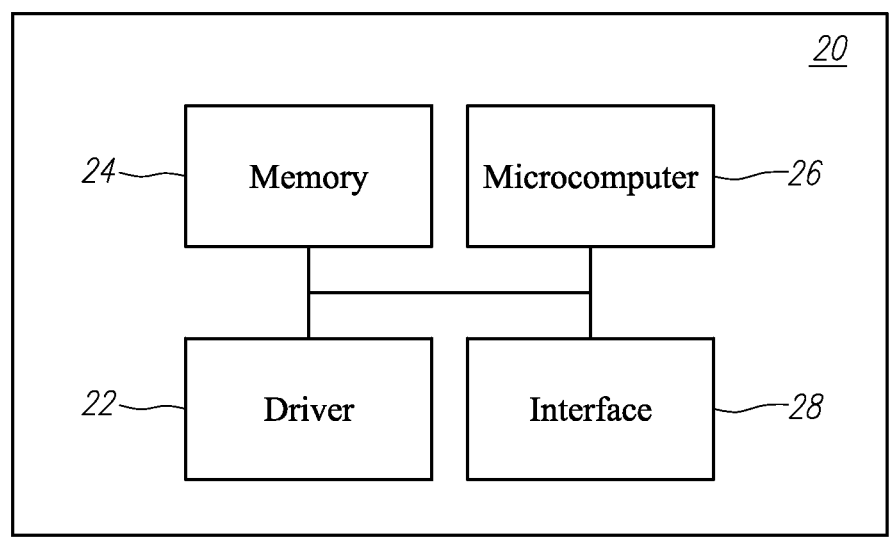
FIG. 2 shows an example of a microcontroller that is constructed according to an aspect of the disclosure.

FIG. 2 shows an example of the microcontroller 20 constructed according to an aspect of the disclosure. The microcontroller 20 comprises a microcomputer 26, a memory 24 and an interface 28. The microcontroller 20 may include a driver 22 that drives an atomizer (not shown). The driver 22 may include, e.g., a pulse-width modulator (PWM) or signal generator. The microcomputer 20 is configured to execute a computer program, which may be stored externally or in the memory 24, to control operations of the eCig (e.g., eCig 10, shown in FIG. 1), including activation (and deactivation) of the heating element. The memory 24 includes a computer-readable medium that may store one or more segments or sections of computer code to carry out the processes described in the instant disclosure. Alternatively (or additionally) code segments or code sections may be provide on an external computer-readable medium (not shown) that may be accessed through the interface 28.

It is noted that the microcontroller 20 may include an application specific integrated circuit (IC), or the like, in lieu of the microcomputer 26, driver 22, memory 22, and/or interface 28.

The microcontroller may be configured to log medium flow data, including mass flow, volume flow, velocity data, time data, date data, flow duration data, and the like, that are associated with the medium flow. The medium may comprise an aerosol, a gas (e.g., air), a liquid, or the like. The microcontroller may be configured not only to turn ON/OFF a heater based on such data, but to also adjust control parameters such as heater PWM or amount of liquid solution dispensed onto a heating surface. This control may be done proportionally to the flow data or according to an algorithm where flow data is a parameter. In addition, the microcontroller may use flow data to determine flow direction and restrict or limit false activation of the heater in case the user accidentally blows into the eCig 10.

Figure 3:
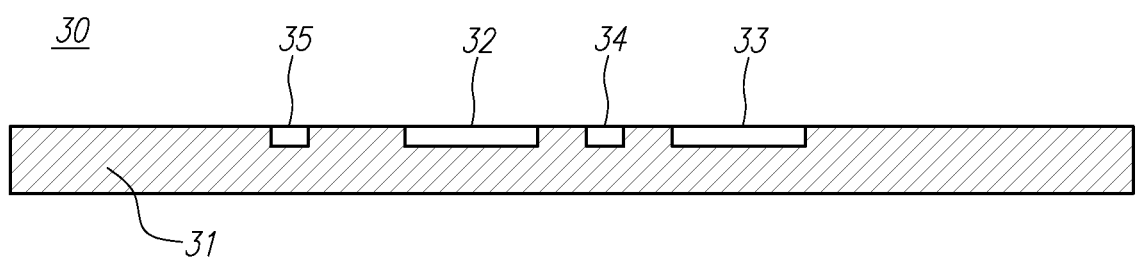
FIG. 3 shows an example of a flow sensor that is constructed according to an aspect of the disclosure.

FIG. 3 shows an example of a flow sensor 30 that is constructed according to an aspect of the disclosure. The flow sensor 30 comprises a substrate 31 and a thermopile (e.g., two or more thermocouples), including an upstream thermopile (or thermocouple) 32 and a downstream thermopile (or thermocouple) 33. The substrate 31 may include a thermal isolation base. The flow sensor 30 may comprise a heater element 34. The flow sensor 30 may comprise a reference element 35. The heater element 34 may include a heater resistor. The reference element 35 may include a reference resistor.

As seen in FIG. 3, the thermopiles 32, 33 may be symmetrically positioned upstream and downstream from the heater element 34. The heater element 34 heats up the hot junctions of the thermopiles 32, 33. In response, each of the thermopiles 32, 33 generates an output voltage that is proportional to the temperature gradient between its hot and cold junctions (the "Seebeck" effect). The hot junctions of the thermopiles 32, 33 and the heater element 34 may reside on the thermal isolation base. Mass air flow sensor signal conditioning may be composed of various forms of filters or gain amplifiers. Filters may be used to eliminate noise before or after signal amplification, thereby reducing sensitivity to unwanted environmental noises or pressure changes. Filtering can be accomplished using low pass, high pass, band pass, or a combination thereof. Signal gain amplification may be accomplished by employing electronic amplification on the upstream or downstream thermopile signals, or a combination thereof. Amplification of upstream or downstream thermopile signals may use a single state or multiple cascaded stages for each signal, or combination of these signals to form a sum or difference. The amplifier circuit may include means to introducing a signal offset. The amplifier may include transistors, operational amplifiers, or other integrated circuits.

Figure 4A:
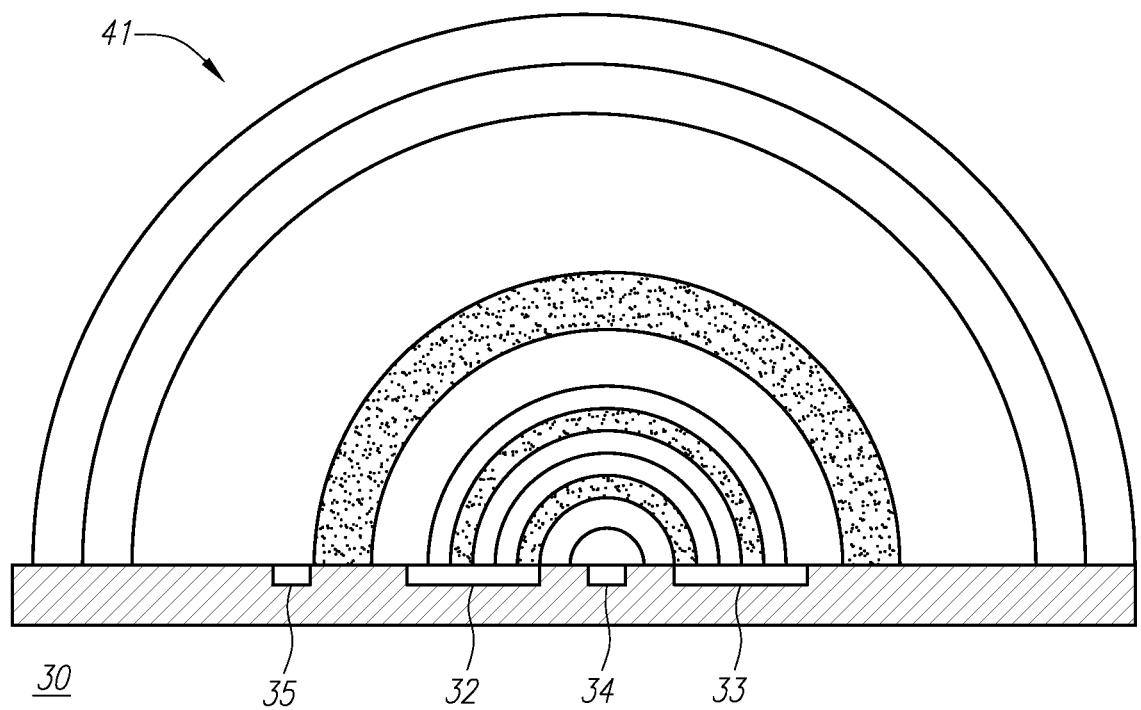
FIGS. 4A and 4B show examples of temperature profiles as a function of airflow movement.
Figure 4B:
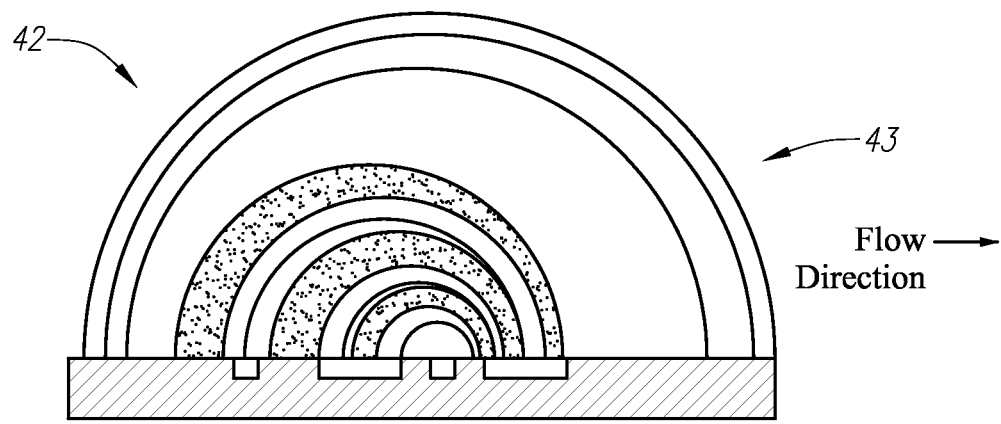

FIGS. 4A and 4B show examples of temperature profiles 41, 42 as a function of airflow movement Referring to FIGS. 3, 4A and 4B, during operation, when the medium is static, the temperature profile 41 upstream and downstream from the heating element 34 is substantially symmetric (shown in FIG. 4A). When the medium (e.g., aerosol) flows, the temperature profile 42 skews in the flow direction due to heat transport of the flowing medium, causing changes in the outputs of the thermopiles 32, 33. Heat transport is proportional to mass flow and heat capacity of the medium. Therefore, the flow sensor 30 measures the mass flow of the medium.

The reference element 35 may be placed next to the cold junction of the upstream thermopile 32 to provide data for temperature compensation.

Referring to FIGS. 1-3, the microcontroller 20 and flow sensor 30 may be provided in the cartridge 14 or the body 18 of the eCig 10. The eCig 10 may include multiple microcontrollers 20 and/or flow sensors 30. The flow sensor 30 may be positioned in a medium flow channel in the eCig 10, so as to detect and measure medium flow (e.g., air flow, aerosol flow, liquid flow, or the like) when a user puffs (or draws) on the mouthpiece of the eCig 10. For instance, a flow sensor 30 may be placed near the air inlet, near the aerosol outlet, in an air channel, or the like, in the eCig 10.

In order to minimize battery drain during operation, the microcontroller 20 may perform an adaptive algorithm that senses medium flow in the region of the flow sensor 30 by, e.g., driving and heating the heating element 34 in short bursts, using infrequent intervals and receiving the sensor signals from the thermopiles 32, 33, and, then, when a puff is detected (e.g., medium flowing above a predetermined threshold), switching to a more frequent cycle of driving the heating element 34 and receiving the sensor signals from the thermopiles 32, 33. By way of example, an infrequent cycle may comprise a 10 ms pulse every second and a frequent cycle may comprise a 10 ms pulse every 50 ms.

The eCig 10 may include an ON/OFF sensor, such as, for example: a capacitive sensor (not shown) that detects when a user contacts the cartridge 14 (e.g., user's finger or lips) and/or body 18 (e.g., user's fingers); a temperature sensor (not shown) that detects user contact (e.g. finger or lips) of the cartridge 14 and/or body 18; a pressure sensor (not shown) that detects a force applied to cartridge 14 and/or body 18 (e.g., squeeze by fingers or lips); an inertia sensor (not shown) that senses movement of the eCig 10; and the like. In response to an ON signal from the ON/OFF sensor, the microcontroller 20 may be awoken (e.g., from a sleep mode) to drive the flow sensor 20 at a higher frequency cycle (e.g., a 50 ms cycle) so as to minimize any delay between user draw on the eCig 10 and delivery of the aerosol. In response to an OFF signal from the ON/OFF sensor, or after a predetermined time of inactivity, the microcontroller 20 may be set to a sleep mode to save battery life. In the sleep mode, the flow sensor may 20 may be driven at a low frequency cycle (e.g., a 1 sec cycle).

The flow sensor 30 is suitable for measurement of liquid flow, gas flow, and differential pressure applications. The flow sensor 30 is sensitive at very low flow rates and pressure levels and does not have significant offset or offset drift due to its differential nature. The flow sensor 30 provides for fast response and is resistant to vibration and pressure shock. The sensor 30 is resistant to corrosive gases/liquids and abrasive wear. The flow sensor 30 allows for implementation of simplified signal conditioning circuits (FIGS. 6A & 6B) in, e.g., the eCig 10 (shown in FIG. 1).

According to an aspect of the disclosure, the thermopiles and heater may be used to determine temperature. For example, when there is no air flow, the heater may be turned ON in order to generate a known signal. The thermopiles would respond to the known heater input. This response would be impacted by the ambient temperature and may be determined. In this regard, rather than looking at a differential signal, one would look at the signal from only one of the thermopiles.

Figure 5:
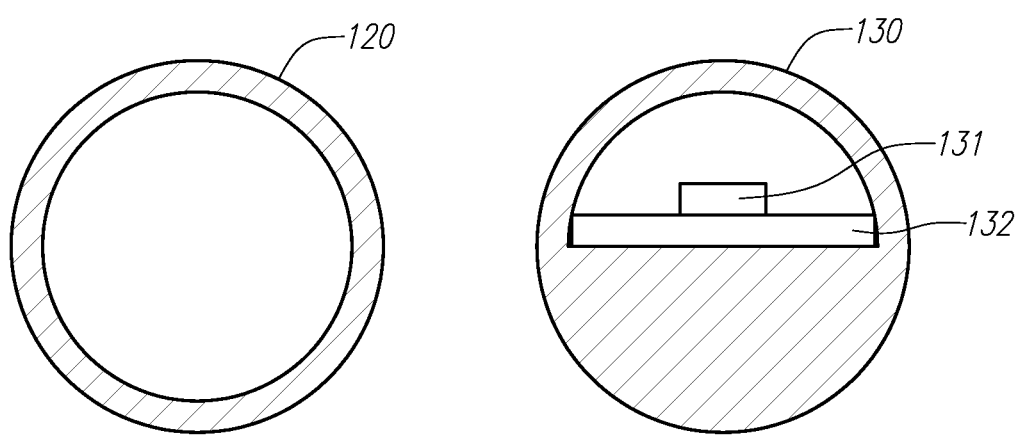
FIG. 5 shows an example of a flow channel according to the principles of the disclosure.

FIG. 5 shows an example of a flow channel according to the principles of the disclosure. As seen in FIG. 5, the flow channel may be shaped in the vicinity of the sensor so as to direct a majority of flow over the sensing surface, thus increasing the sensitivity of the system. As illustrated in FIG. 5, the housing 120 of a normal cross-section is mostly open. In the cross-section near a sensor 131, a housing 130 is restricted such that a pcb 132 and the sensor 131 are positioned so that a majority of the flow moves over the sensor 131.

As an alternative way to determine ambient temperature, a thermistor or other temperature measuring sensor could be placed in the airflow. The signal from this sensor could be used alone or in conjunction with a MAF in order to adjust the heater control signal or disable the eCig in response to temperature limits. One may choose to disable the eCig, for example, if high temperatures may cause juice spoilage or if battery safety/performance is impacted by temperature extremes.

It is noted that a reference resistor can be used to determine ambient environment and either adjust the heater via PWM or disable the heater when storage/operation temperature limits are exceeded.

Because operating the mass airflow sensor may place an electrical current demand on the battery, it may be desirable to include a secondary means by which to initiate the operation of the mass airflow sensor. One such means of accomplishing this is possible in the rechargeable configuration of the eCig, a configuration where the liquid and heater are housed in a separate and detachable housing from the sensor and the battery. When the unit housing, the liquid, and the heater are connected to the portion housing the sensor and the battery, this connection event may be detected by the microcontroller, which may also be housed with the sensor. By way of example, the heater, which electronically behaves as a resistor, may complete a circuit that triggers an interrupt signal to be caused on an input pin of the microcontroller. This interrupt event could then cause the microcontroller to activate the previously inactive mass airflow sensor and begin to take readings using the mass airflow sensor. When the portion housing the liquid and the heater are detached from the portion housing the sensor and the battery, the microcontroller may then deactivate the mass airflow sensor.

As mentioned in the previous example, the initiation of the mass airflow sensor could be accomplished by using the heater resistance to complete a circuit, however, this is not the only means to accomplish such a trigger event. Other ways of accomplishing such a trigger event include incorporating a dedicated physical connection or trace that completes a circuit, a capacitor that discharges or charges when the connection is made, and an integrated circuit that establishes communication with the microcontroller when the connection is made.

Figure 6A:
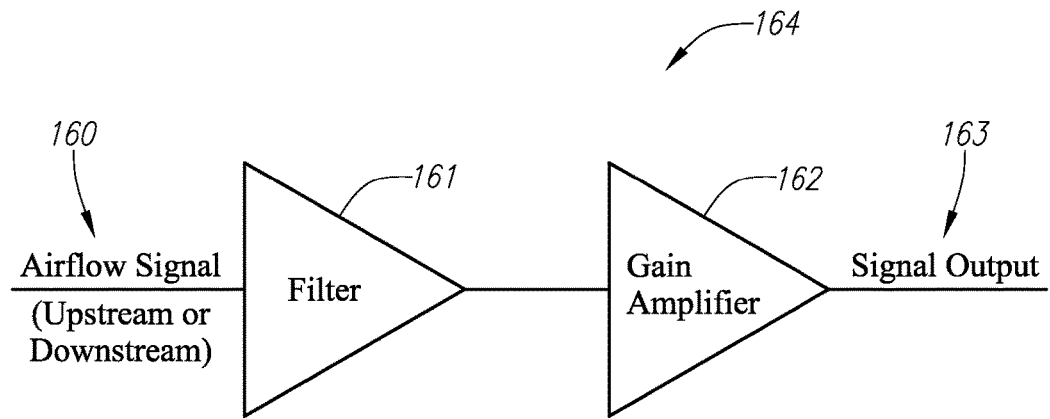
FIGS. 6A & 6B show an example of signal amplification and filtering through a single amplifier or multiple amplifiers.
Figure 6B:
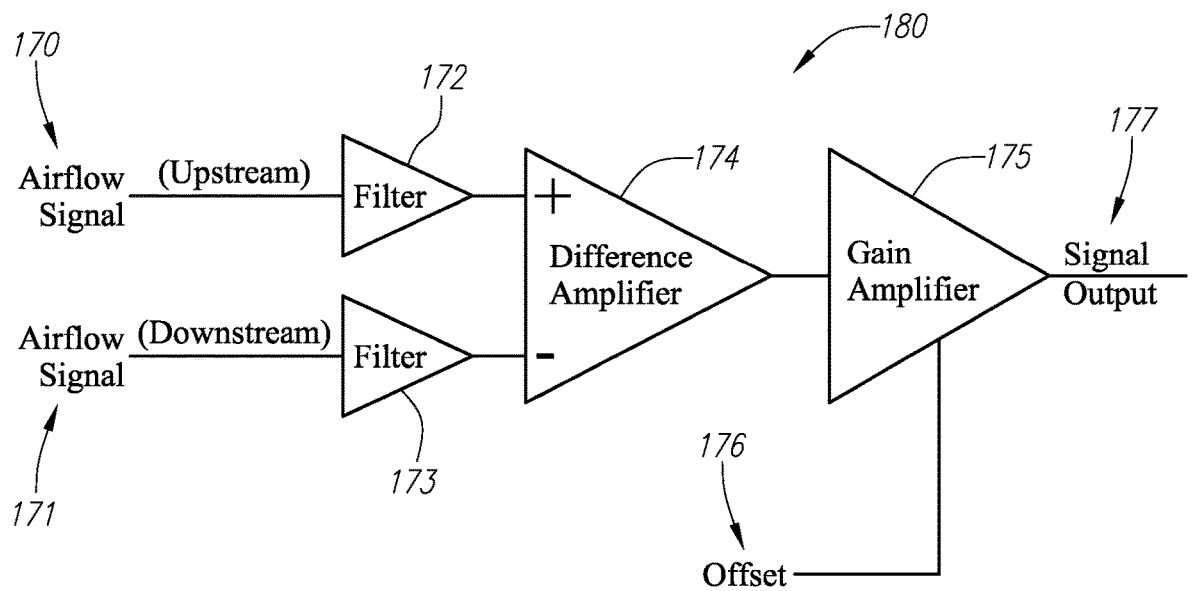

FIGS. 6A and 6B illustrate an example of a single amplifier with a filter 164 and a difference amplifier and filters for upstream and downstream, with offset 180. As shown in the single amplifier with a filter 164 in FIG. 6A, the airflow signal 160 passes through a filter 161 and a gain amplifier 162 before a signal output 163 is transmitted. The difference amplifier and filters for upstream and downstream, with offset 180 shown in FIG. 6B comprises an upstream airflow signal 170 and a downstream airflow signal 171. The upstream airflow signal 170 passes through a first filter 172 and the downstream airflow signal passes through a second filter 173. The outputs of the first and second filters 171,172 then enter a difference amplifier 174. A signal is then output from the difference amplifier 174 and enters a gain amplifier 175 along with an offset 175. The gain amplifier 175 then outputs a signal output 177.

Figure 7:
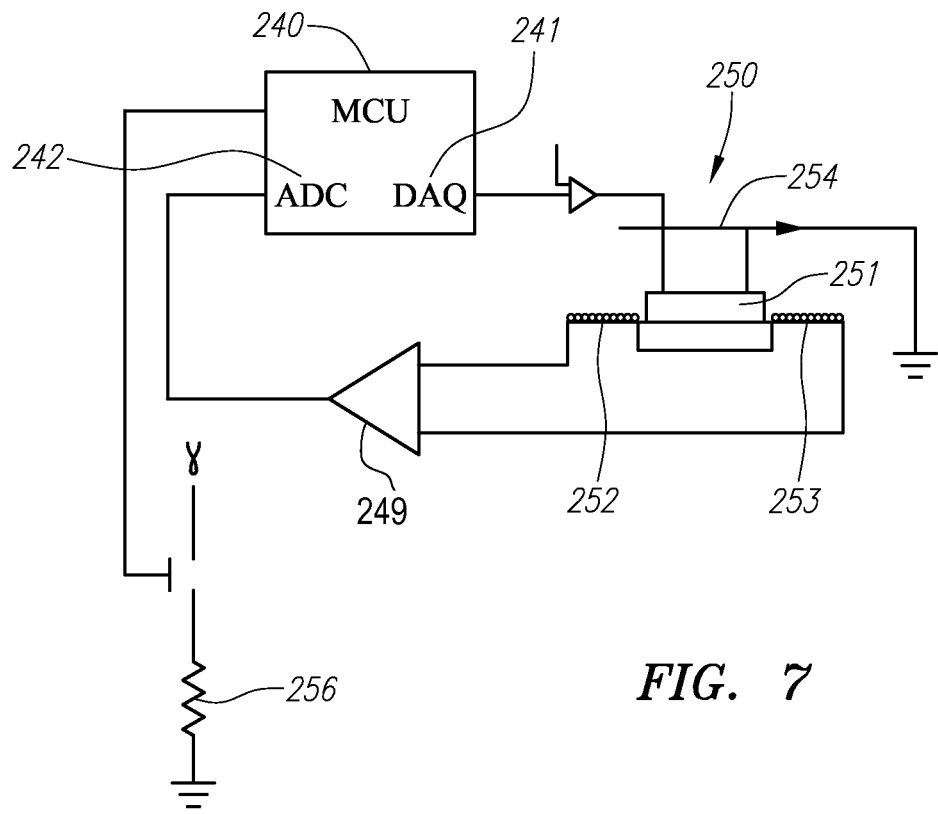
FIG. 7 is an electrical diagram of an eCig comprising a first and second thermopile.

FIG. 7 illustrates an electrical diagram of an embodiment of the disclosure comprising a first thermopile 252 and a second thermopile 253. The eCig depicted in FIG. 7 comprises a microcontroller 240, a mass airflow sensor 250, an amplifier 249, and a heater 256. The mass airflow sensor 250 comprises a mass airflow heater 251, a first thermopile 252, and a second thermopile 253. The electrical diagram further illustrates the direction of airflow 254 over the mass airflow heater 251 and the first and second thermopiles 252, 253. The microcontroller 240 can comprise a data acquisition circuit 241, and an analog-to-digital converter 242. The data acquisition circuit 241 can log and transmit data such as temperature of the heater 256, the number of times the heater 256 has been activated in a certain time, the length of time the heater 256 had been activated, and other information. A more detailed description of data acquisition and transmission can be found in commonly assigned U.S. Provisional Application No. 61/907,239 filed 21 Nov. 2013, the entire disclosure of which is hereby incorporated by reference as though fully set forth herein. The analog-to-digital converter 242 can output information about the eCig to the microcontroller 240, the data acquisition circuit 241, and other devices and sensors that may be present on the microcontroller 240 or otherwise connected to the eCig.

Figure 8:
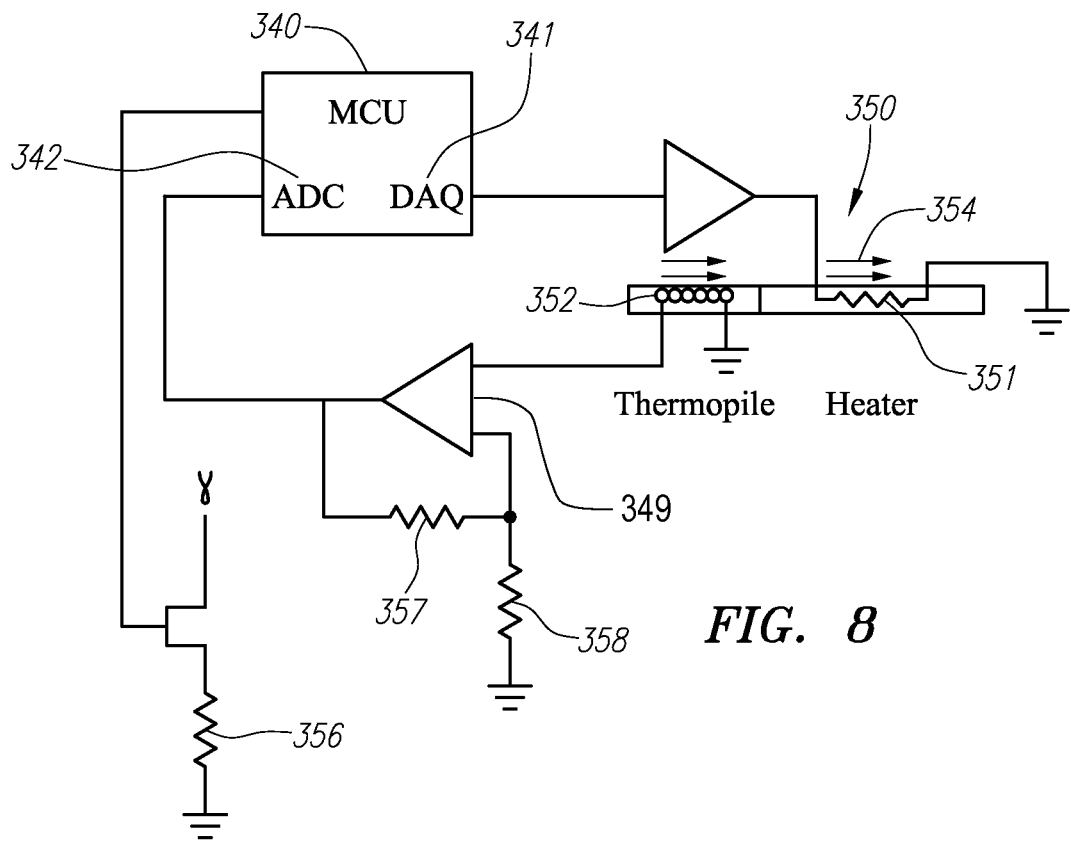
FIG. 8 is an electrical diagram of an eCig comprising one thermopile.

FIG. 8 illustrates an electrical diagram of another embodiment of the disclosure comprising one thermopile 352. The eCig depicted in FIG. 8 comprises a microcontroller 340, a mass airflow sensor 350, an amplifier 349, and a heater 356. The mass airflow sensor 350 comprises a mass airflow heater 351 and a thermopile 352. The electrical diagram further illustrates the direction of airflow over the heater 354 and the thermopile 352. The microcontroller 340 can comprise a data acquisition circuit 341, and an analog-to-digital converter 342. The data acquisition circuit 341 can log and transmit data such as temperature of the heater 356, the number of times the heater 356 has been activated in a certain time, the length of time the heater 356 had been activated, and other information. The analog-to-digital converter 342 can output information about the eCig to the microcontroller 340, the data acquisition circuit 341, and other devices and sensors that may be present on the microcontroller 340 or otherwise connected to the eCig. In one embodiment, the eCig can also comprise feedback and gain resistors 357, 358.

Figure 9:
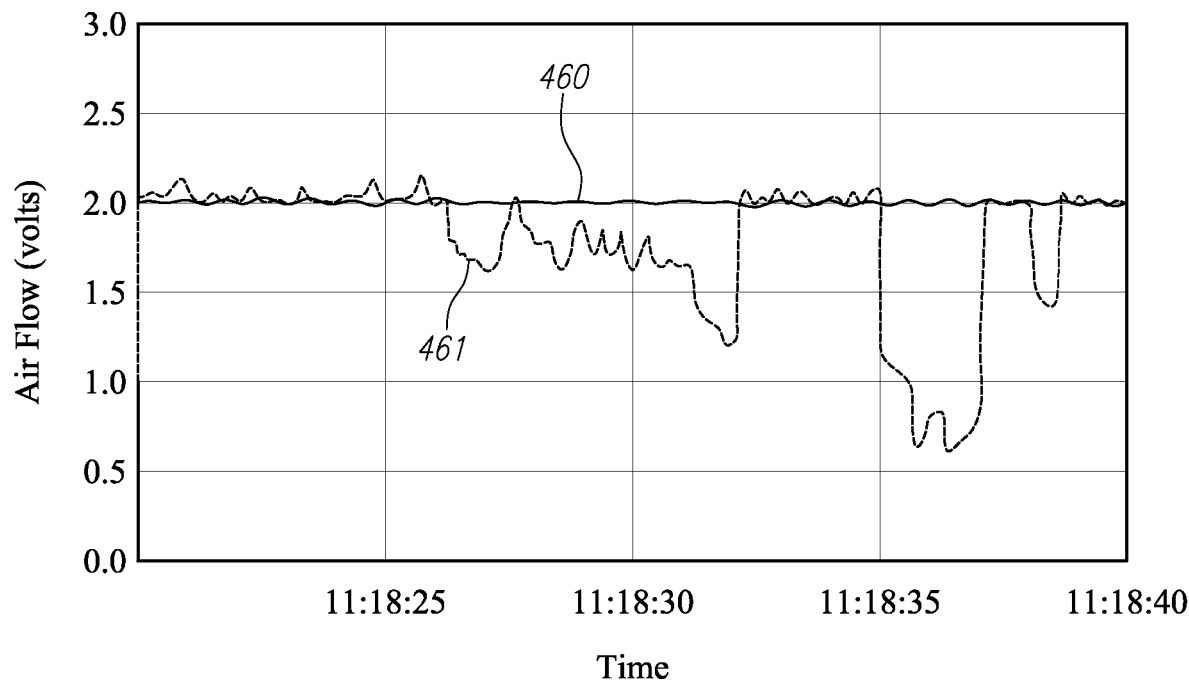
FIGS. 9-11 are graphs of an embodiment of the output of a reference signal and an airflow sensor according to the disclosure.
Figure 10:
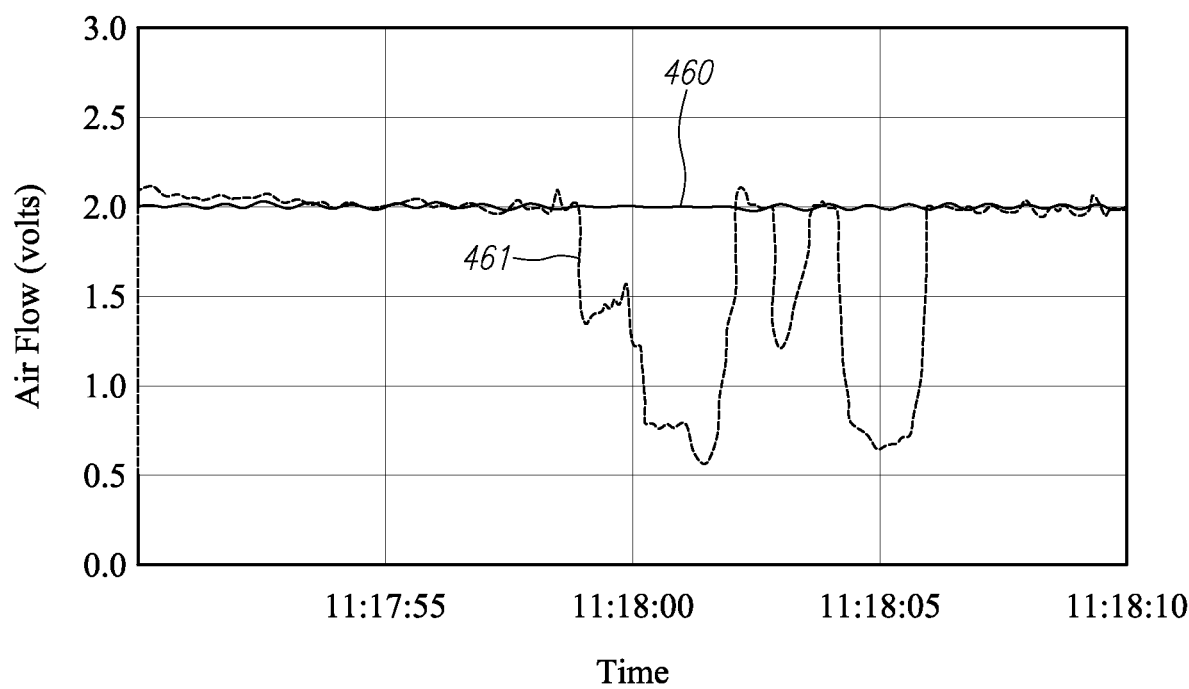
Figure 11:
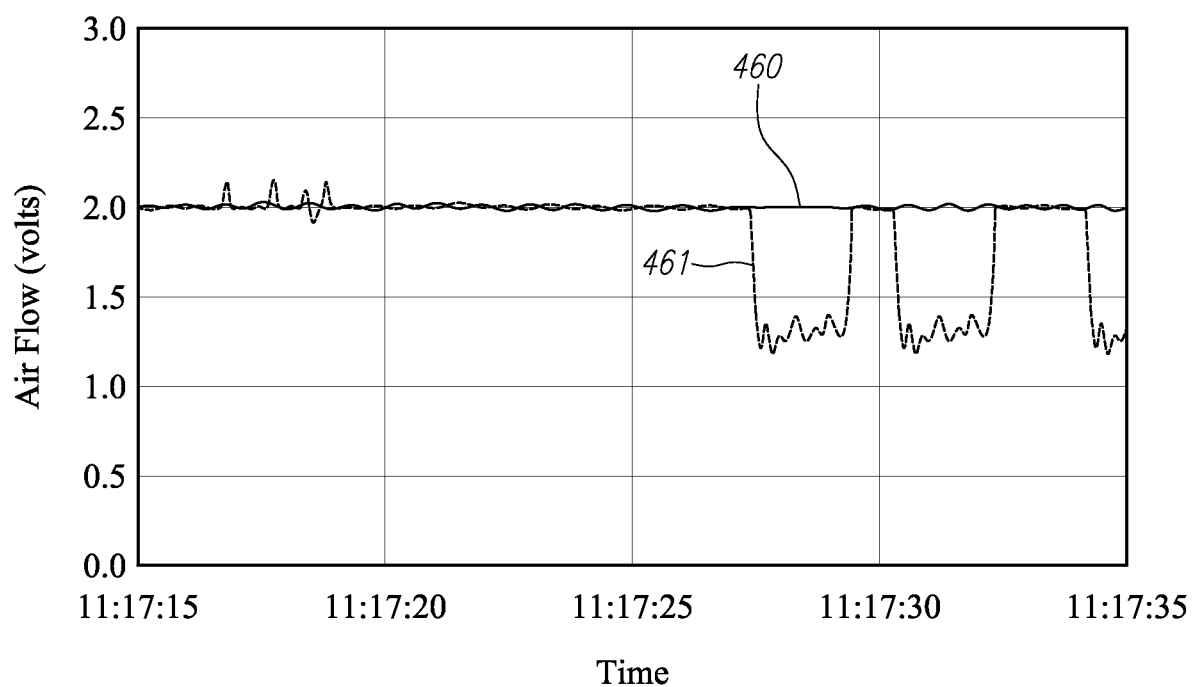

FIGS. 9-11 illustrate graphical representations of the outputs of the reference signal and the mass air-flow sensor as discussed throughout the disclosure. In the illustrated embodiment a reference signal 460 is normalized to a baseline of 2.0 volts. In other embodiments, the reference signal 460 can be normalized to a different baseline. The reference signal 460 is composed of a moving average of the airflow signal when no airflow is present. This can establish a no-flow baseline condition. The output of the mass air flow sensor in relation to the reference signal 461 can then be conditioned to output a baseline of 2.0 volts. When the output of the mass airflow sensor changes under a predetermined threshold, the reference signal 460 will normalize that change to the baseline. This can allow for subtle changes to occur in the environment, such as temperature change or battery depletion, without the output of the mass air flow sensor in relation to the reference signal 461 to drift. When the output signal changes above a predetermined threshold, the reference signal 460 will stay at the previously normalized baseline and the output of the mass air flow sensor in relation to the reference signal 461 will change proportionally to the amount of fluid flowing over the sensor. When a fluid flow moves over the mass air flow sensor, the output of the mass air flow sensor can then change proportionally to the volume or velocity of the fluid moving past the sensor.

When the reference baseline is stressed, the output of sensor can change, but at a rate below the predetermined threshold, and can cause the microcontroller to normalize the reference signal 460 and the output of the mass air flow sensor in relation to the reference signal 461 to the desired baseline. The stress to the mass airflow sensor can be either electrical or mechanical in nature. The stress to the mass airflow sensor can also occur because of a change in the ambient temperature of the fluid flowing over the mass air flow sensor. In some embodiments, by determining the amount of fluid or air flow over the sensor, the microcontroller can vary the power output to the atomizer or heater coil. By varying the power output, the microcontroller can better control the temperature of the atomizer or heater coil. In one embodiment, the microcontroller can use the data from the flow sensor to run the eCig heater at a constant temperature over varying rates of flow. This constant temperature can result in a better experience for a user, as the flavorant or juice within the cartomizer or eCig will be vaporized at a constant temperature.

Figure 12:
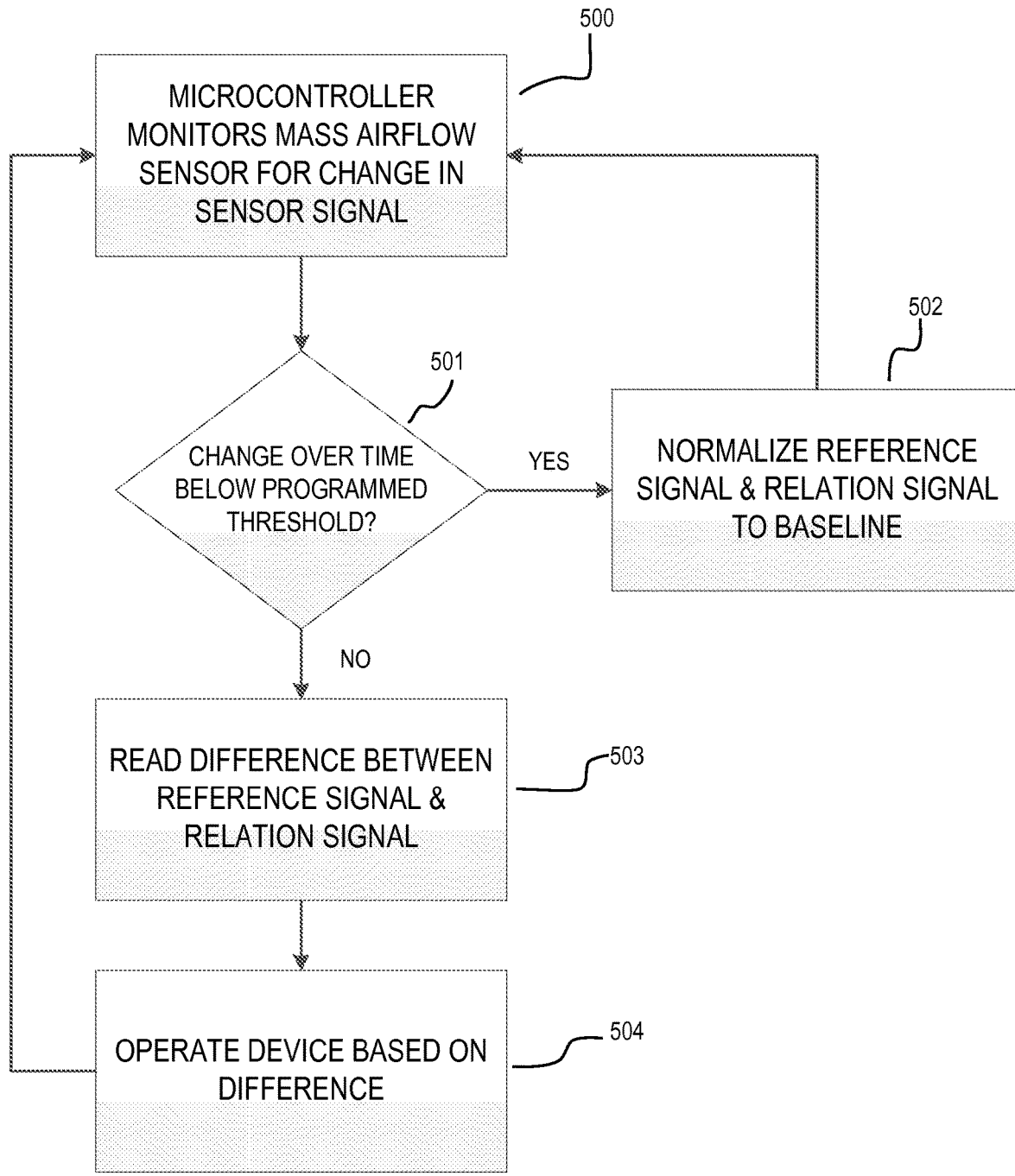
FIG. 12 is a flowchart illustrating one embodiment of a process for interpreting signals according to the disclosure.

FIG. 12 illustrates a flow-chart of the process by which the microcontroller or other component can interpret signals from the mass airflow sensor or other device. In step 500 a microcontroller can monitor a sensor signal sent from the mass airflow sensor. When the microcontroller monitors a change in the sensor signal that is being monitored in step 500, the microcontroller can determine if the change in the sensor signal is below a programmed threshold 501. If the change in the sensor signal over a length of time is below the programmed threshold the microcontroller or other component can alter a reference signal and a relation signal to a predetermined baseline 502. In one embodiment the reference signal can be set to a baseline reading of 2.0 volts. The microcontroller than continues to monitor the mass airflow sensor for a change in the sensor signal 500. If the change in the sensor signal over time is above a programmed threshold 501, then the microcontroller or other component reads the difference between the reference signal and the relation signal 503. In step 504, the microcontroller or other component can operate a device, sensor, or other component according to the difference between the reference signal and the relation signal. The process then goes back to step 500 and the microcontroller or other component continues to monitor the mass airflow sensor for a change in the sensor signal over time.

In one embodiment, the microcontroller can determine an amount of air flow that is passing over the mass airflow sensor by the difference between the reference signal and the relation signal. In another embodiment, the microcontroller can determine an amount of air flow that is passing through the body by the difference between the reference signal and the relation signal. Once the microcontroller determines or estimates an amount of air flow that is passing over the mass airflow sensor or through the body, the microcontroller can then vary the output of energy that is sent to the atomizer or heater. The microcontroller can vary the output of energy to keep the temperature of the atomizer or heater at a constant temperature or to otherwise control an aspect of the atomizer or heater.

The instant disclosure may be implemented to measure and monitor mass flow, differential pressure, and/or air velocity in applications such as, e.g., heating ventilation and air conditioning (HVAC), automotive, medical respirators, medical ventilators, diesel generators and engines (e.g., to monitor fuel consumption), drug delivery, biomedical analytical tools, and the like.

A "computer" or "microcomputer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, or the like, or an array of processors, microprocessors, central processing units, general purpose computers, or the like.

A "computer-readable medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a flexible disk, hard disk, magnetic tape, any other magnetic medium, any other optical medium, a RAM, a PROM, an EPROM, a FLASH-EEPROM, any other memory chip or cartridge, a carrier wave as described hereinafter, or any other medium from which a computer can read.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols known in the art as of the date of this writing.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

What is claimed is:

1. An electronic cigarette comprising:
a body;
an atomizer within the body, wherein the atomizer is configured to atomize a liquid solution;
a microcontroller configured to generate a reference baseline;
a power supply within the body and electrically connected to the microcontroller and the atomizer; and
a mass air flow sensor electrically connected to the microcontroller, wherein the mass air flow sensor comprises a substrate and a thermopile, wherein the mass air flow sensor is configured to generate a reference signal and to send signals to the microcontroller of medium flow,
wherein the microcontroller is configured to turn on the atomizer based on the signals from the mass air flow sensor, and wherein the microcontroller is set from a sleep mode to a non-sleep mode in response to a second signal, the microcontroller is set from the non-sleep mode to the sleep mode in response to a third signal, and the mass air flow sensor is driven at a low frequency cycle at the sleep mode, compared with the non-sleep mode, and wherein the reference baseline is created from the reference signal during the non-sleep mode and wherein the reference signal is normalized to the reference baseline when a change per time of the reference signal during the non-sleep mode is below a predetermined threshold.

2. The electronic cigarette according to claim 1, wherein the microcontroller is further configured to compare an output of the mass airflow sensor to the reference baseline.

3. The electronic cigarette according to claim 1, wherein the atomizer comprises a heater.

4. The electronic cigarette according to claim 1, wherein the microcontroller comprises a microcomputer, a memory, and an interface.

5. The electronic cigarette according to claim 1, wherein the microcontroller is configured to use flow data to determine flow direction.

6. The electronic cigarette according to claim 5, wherein the microcontroller is further configured to limit activation of a heater based off of the direction of airflow.

7. The electronic cigarette according to claim 1, wherein the microcontroller is configured to log medium flow data.

8. The electronic cigarette according to claim 1, wherein the microcontroller is configured to use flow data to determine an amount of air flowing through the body.

9. The electronic cigarette according to claim 8, wherein the microcontroller is further configured to vary an output of power to the atomizer based off the amount of air flowing through the body.

10. An electronic cigarette comprising:
a first housing and a second housing;
an atomizer within the first housing, wherein the atomizer is configured to atomize a liquid solution;
a microcontroller within the second housing and comprising a data acquisition circuit and an analog-to-digital converter, wherein the microcontroller is configured to generate a reference baseline;

a power supply within the second housing and configured to be electrically connected to the microcontroller and the atomizer; and a mass air flow sensor electrically connected to the microcontroller and configured to generate a reference signal, wherein the mass air flow sensor comprises a substrate and a thermopile, wherein the mass air flow sensor is configured to send signals to the microcontroller of medium flow, wherein the microcontroller is configured to turn on the atomizer based on the signals from the mass air flow sensor, and wherein the microcontroller is set from a sleep mode to a non-sleep mode in response to a second signal, the microcontroller is set from the non-sleep mode to the sleep mode in response to a third signal, the mass air flow sensor is driven at a low frequency cycle at the sleep mode, compared with the non-sleep mode, and wherein the reference baseline is created from the reference signal during the non-sleep mode and wherein the reference signal is normalized to the reference baseline when a change per time of the reference signal during the non-sleep mode is below a predetermined threshold, and wherein the first housing is configured to be coupled to the second housing.

11. The electronic cigarette according to claim 10, wherein the microcontroller is further configured to compare an output of the mass air flow sensor to the reference baseline.

12. The electronic cigarette according to claim 10, wherein the atomizer comprises a heater.

13. The electronic cigarette according to claim 10, wherein the microcontroller comprises a microcomputer, a memory, and an interface.

14. The electronic cigarette according to claim 10, wherein the microcontroller is configured to used flow data to determine flow direction.

15. An electronic cigarette comprising:

an atomizer configured to atomize a liquid solution;

a microcontroller comprising a data acquisition circuit and an analog-to-digital converter, wherein the microcontroller is configured to generate a reference baseline;

a power supply electrically connected to the microcontroller and the atomizer; and a mass air flow sensor comprising a thermopile and a mass air flow heater, and wherein the mass air flow sensor is electrically connected to the microcontroller and configured to generate a reference signal, wherein the mass air flow sensor is configured to send signals to the microcontroller of medium flow, wherein the microcontroller is configured to turn on the atomizer based on the signals from the mass air flow sensor, and wherein the microcontroller is set from a sleep mode to a non-sleep mode in response to a second signal, the microcontroller is set from the non-sleep mode to the sleep mode in response to a third signal, and the mass air flow sensor is driven at a low frequency cycle at the sleep mode, compared with the non-sleep mode, and wherein the reference baseline is created from the reference signal during the non-sleep mode and reference signal is normalized to the reference baseline when a change per time of the reference signal during the non-sleep mode is below a predetermined threshold.

16. The electronic cigarette according to claim 15, wherein the atomizer comprises an atomizer heater.

17. The electronic cigarette according to claim 15, wherein the microcontroller comprises a microcomputer, a memory, and an interface.

* * * * *